United States Patent
LeBerthon

(10) Patent No.: US 9,694,128 B1
(45) Date of Patent: Jul. 4, 2017

(54) DEVICE AND METHOD FOR ADMINISTERING AN ANTI-CANCER SUBSTANCE

(76) Inventor: Brian LeBerthon, Arcadia, CA (US)

( * ) Notice: Subject to any disclaimer, the term of this patent is extended or adjusted under 35 U.S.C. 154(b) by 0 days.

(21) Appl. No.: 13/032,951

(22) Filed: Feb. 23, 2011

Related U.S. Application Data

(60) Provisional application No. 61/307,635, filed on Feb. 24, 2010.

(51) Int. Cl.
*A61M 37/00* (2006.01)
*A61M 1/36* (2006.01)
*A61M 1/34* (2006.01)

(52) U.S. Cl.
CPC ............ *A61M 1/36* (2013.01); *A61M 1/3687* (2013.01); *A61M 1/3472* (2013.01); *A61M 1/362* (2014.02)

(58) Field of Classification Search
CPC ...... A61M 1/362; A61M 1/3679; A61M 1/16; A61M 1/3689; A61M 1/3687; A61M 1/36; A61M 1/3615
See application file for complete search history.

(56) References Cited

U.S. PATENT DOCUMENTS

| | | | |
|---|---|---|---|
| 4,350,156 A * | 9/1982 | Malchesky et al. | 604/6.04 |
| 4,605,394 A * | 8/1986 | Skurkovich | 604/4.01 |
| 4,844,893 A | 7/1989 | Honsik et al. | |
| 4,955,857 A * | 9/1990 | Shettigar | 604/6.06 |
| 5,209,717 A | 5/1993 | Schmoll et al. | |
| 5,628,727 A * | 5/1997 | Hakky et al. | 604/6.08 |
| 5,649,904 A * | 7/1997 | Gianni | 604/5.01 |
| 5,676,644 A * | 10/1997 | Toavs et al. | 604/6.11 |
| 5,874,308 A * | 2/1999 | Kilburn et al. | 435/395 |

(Continued)

FOREIGN PATENT DOCUMENTS

WO   WO 2007/011896   * 1/2007

OTHER PUBLICATIONS

Houghton, Alan et al. (Monclonal antibody therapies—a 'constant' threat to cancer, Nature Medicine, 6, 373-374 (2000)).*

(Continued)

*Primary Examiner* — Tatyana Zalukaeva
*Assistant Examiner* — Ariana Zimbouski
(74) *Attorney, Agent, or Firm* — John J. Connors; Connors & Assoc.

(57) ABSTRACT

An anti-cancer substance is administered via the patient's blood ex vivo and in line by establishing a connection between the patient and a device having a chamber containing the anti-cancer substance. The patient's blood in the chamber and the anti-cancer substance interact so that immune cells in the blood (1) are activated to produce an immune response in the patient, or (2) are pre-armed by attaching to the cells antibodies, or (3) both. After activating or pre-arming the cells, the patient's treated blood is returned to the patient. The anti-cancer substance may be within the chamber prior to drawing the patient's blood into the chamber, may be introduced into the chamber after drawing the patient's blood into the chamber, or may be introduced into the chamber concurrent with the introduction of the patient's blood into the chamber. The connection is terminated after returning to the patient's blood including the activated or pre-armed cells.

1 Claim, 4 Drawing Sheets

(56) References Cited

U.S. PATENT DOCUMENTS

| | | | |
|---|---|---|---|
| 6,528,057 B1* | 3/2003 | Ambrus | A61K 35/14 |
| | | | 210/645 |
| 6,855,291 B2 | 2/2005 | Patterson et al. | |
| 7,094,378 B1* | 8/2006 | Goodrich et al. | 422/22 |
| 7,763,243 B2* | 7/2010 | Lum et al. | 424/93.71 |
| 2003/0147812 A1* | 8/2003 | Ueberle | 424/9.52 |
| 2009/0047288 A1* | 2/2009 | Yan | 424/141.1 |
| 2012/0201799 A1* | 8/2012 | Federspiel et al. | 424/93.71 |

OTHER PUBLICATIONS

PCT/US2010/051772, Published PCT applicataion, Apr. 14, 2011, Federspiel, et al.

\* cited by examiner

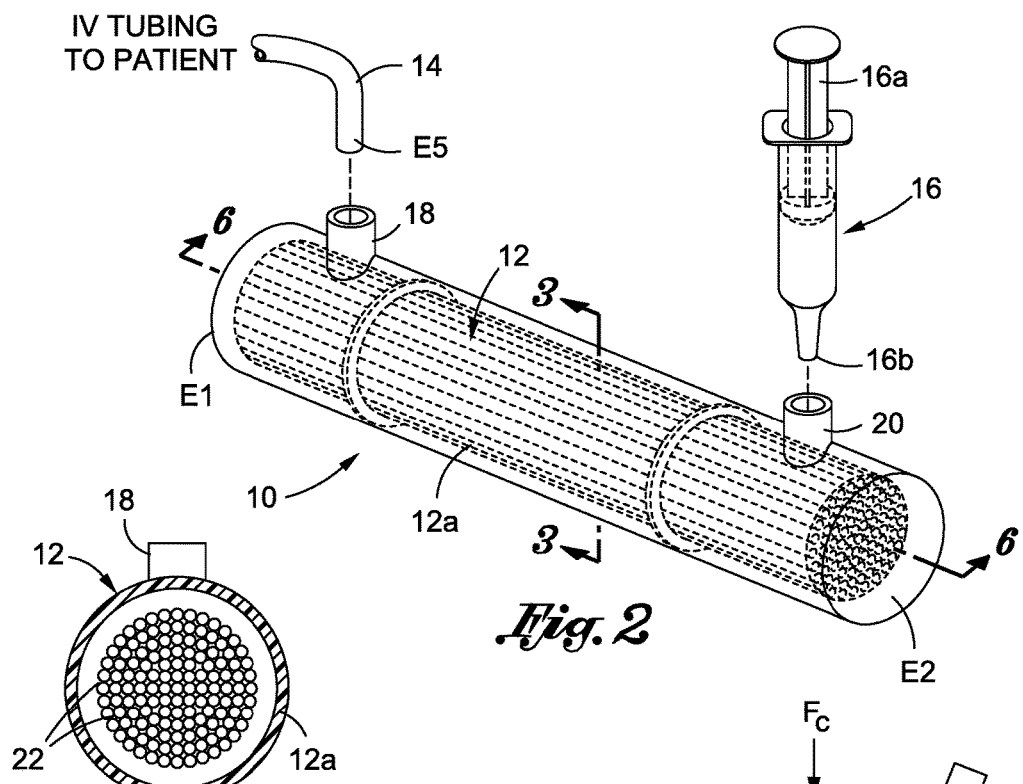
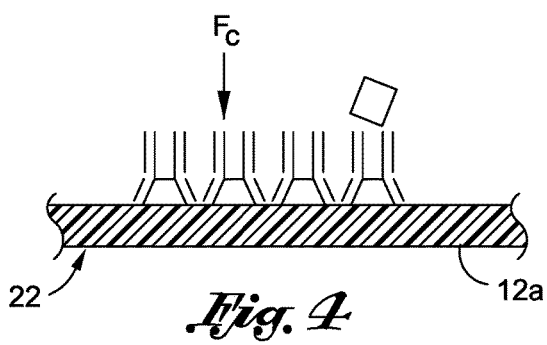
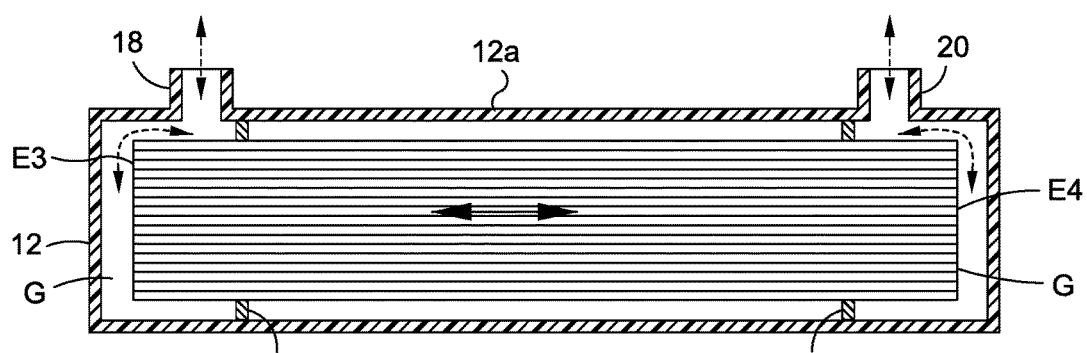

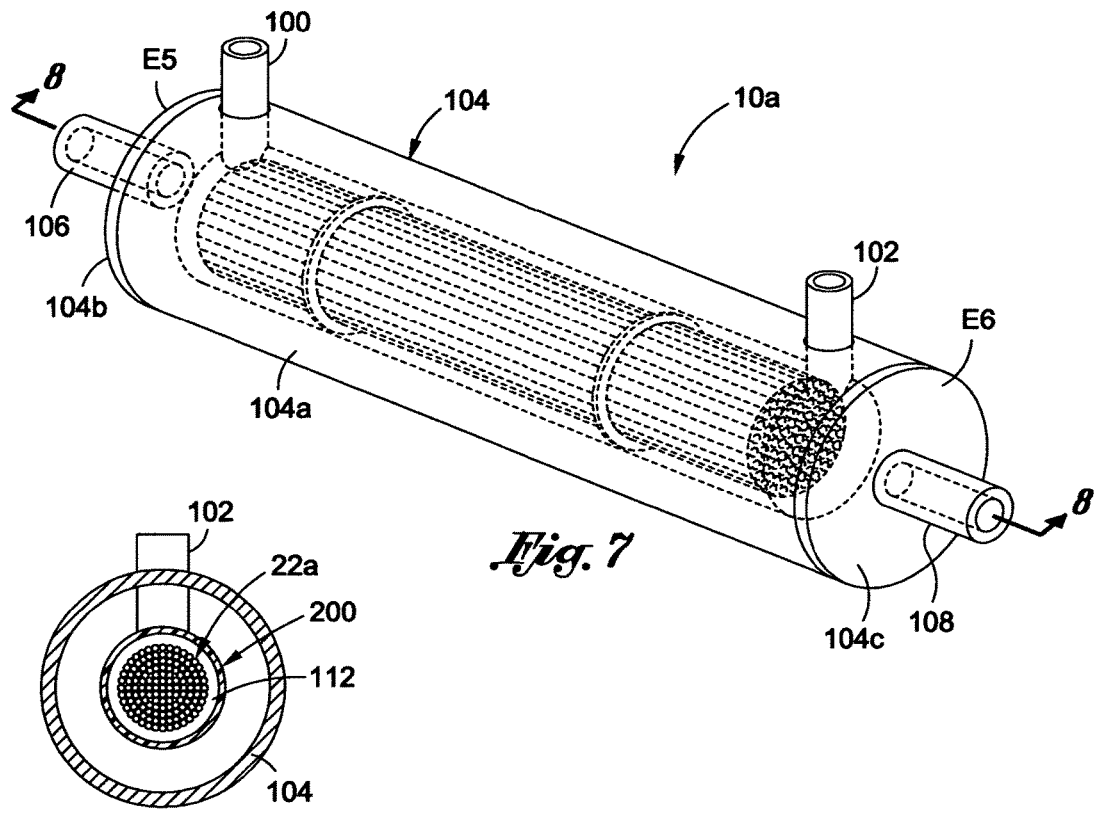
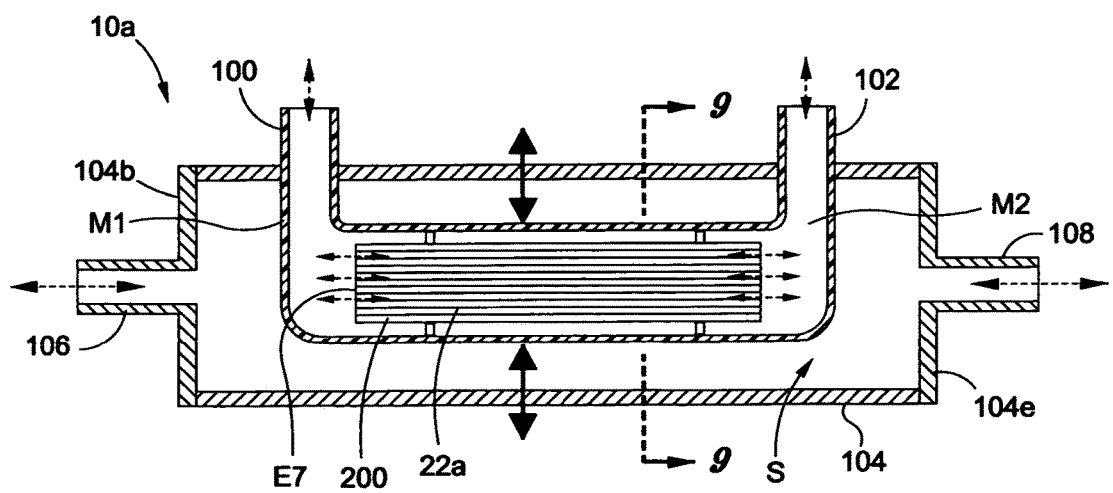

DEVICE AND METHOD FOR ADMINISTERING AN ANTI-CANCER SUBSTANCE

RELATED PATENT APPLICATIONS & INCORPORATION BY REFERENCE

This utility application claims the benefit under 35 USC 119(e) of U.S. Provisional Patent Application No. 61/307,635, entitled "DEVICE AND METHOD FOR ADMINISTERING AN ANTI-CANCER SUBSTANCE," filed Feb. 24, 2010. This related applications is incorporated herein by reference and made a part of this application. If any conflict arises between the disclosure of the invention in this utility application and that in the related provisional application, the disclosure in this utility application shall govern. Moreover, any and all U. S. patents, U. S. patent applications, and other documents, hard copy or electronic, cited or referred to in this application are incorporated herein by reference and made a part of this application.

DEFINITIONS

The words "adjuvant material" mean a substance that activates effector cells (hereinafter defined), usually in a laboratory or vaccine setting, against an antigen (hereinafter defined) that is presented to the effector cells at the same time. An adjuvant material is usually a foreign material that the immune cells seem to regard as noxious. Adjuvant materials stimulate the immune system to operate against an antigen. Such operations may include the activation of antigen-specific effector cells and antigen presenting cells, and may include the generation of antigen specific antibodies.

The word "antibody" or word "antibodies" is a protein or proteins that bind specifically to a particular antigen, and often has immune function.

The word "antigen" is a substance that is bound by antibodies and, under the correct circumstances, can prompt the generation of antibodies and cause an immune response. All molecular structures that can be specifically bound by antibodies are antigens whether or not the interaction between antigen and antibody leads to subsequent responses by the immune system. Immunogenicity and antigenicity are related, but distinct. Immunogenicity is the ability to induce a humoral and/or cell-mediated immune response. Antigenicity is the ability to combine specifically with the final products of the [immune response] (i.e. secreted antibodies and/or surface receptors on T-cells or other effector cells). Although all molecules that have the property of immunogenicity also have the property of antigenicity, the reverse is not true.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

The words "consisting," "consists of," and other forms thereof, are intended to be equivalent in meaning and be closed ended in that an item or items following any one of these words is meant to be an exhaustive listing of such item or items and limited to only the listed item or items.

The words dendritic cell(s) are cells that are associated with antigen presentation. Antigen presentation is the process wherein an antigenic molecule is consumed by a cell, usually by phagocytosis, broken down within the cell, and components of the antigenic molecule are subsequently displayed on the surface of the dendritic cell along with other molecular signals to stimulate and specifically sensitize other cells of the immune system to engender an immune response. These cells may be effector cells or cells capable of directing other cells of the immune system.

The words "effector cell(s)" are cells of the immune system which are responsible for enacting directly or indirectly the ultimate operation of immunity, such as, for example, lysis of tumor cells or phagocytosing (ingesting) targets (cells or other materials) associated with antigens. These cells may include T-cells, NK cells, macrophages, monocytes and granulocytes.

The words "ex vivo" mean taking place in a chamber apart from the patient but while the chamber is connected to a patient's body so blood from the patient flows into the chamber and is returned to the patient without disconnection.

The words "in vitro" mean taking place in a test tube or other vessel apart from the patient and not connected to a patient's body.

The words "in line" mean within a chamber outside a patient's body that is connected to the patient to draw blood into the chamber.

The words "substantially" and "essentially" have equivalent meanings.

BACKGROUND

Cancer in its many forms is uncontrolled growth of abnormal cells in the body. Cancerous cells are frequently referred to as malignant cells and often form tumors. Symptoms of cancer depend on the type and location of the tumor. Various anti-cancer substances having the potential to suppress the cancer's growth or destroy cancer cells are injected into a cancer patient. For example, biotech companies have developed antibodies that attach to effector cells or other targets within a patient's blood or areas accessible to the blood stream that may result in the regression of the cancer, or at least suppression of its growth. Currently, such antibodies are dispersed in a carrier liquid that is administered directly into the vein of a patient. These antibodies may act by different mechanisms, such as by attaching to growth factors, or their receptors, and interfering with growth signals. Such mechanisms may also operate by prohibiting new blood vessel growth into the tumor. Other antibodies attach to various antigens on tumor cells, and are believed to operate by allowing effector cells to localize to the tumor cells and destroy them. Attachment of antibodies to effector cells, however, does not always lead to immediate and complete termination of the cancerous growth or provoke an immune response from the patient. Nevertheless, such attachment is desirable because anti-tumor activity on the part of effector cells is conducted by such attachment of the antibodies. Other anti-cancer substances beside antibodies may interact with a patient's effector cells to provoke an immune response, whether or not any specific antibody attachment occurs. An example of this is interferon, which is known to stimulate effector cells against cancer. Immune responses may be different with different types of cancers, and conceivably in the same tumor type in different patients. Provoking an immune response is a way to enable the patient's own immune system to suppress the growth of the cancer.

SUMMARY

My method and device introduces in line into a patient's blood an anti-cancer substance contained within a chamber.

The anti-cancer substance acts upon immune cells in the patient's blood, which in general are white blood cells (WBC) including, for example, dendritic cells, antigen presenting cells (APC's), and effector cells. My method and device have one or more of the features depicted in the embodiments discussed in the section entitled "DETAILED DESCRIPTION OF SOME ILLUSTRATIVE EMBODIMENTS." The claims that follow define my method and device, distinguishing them from the prior art; however, without limiting the scope of my method and device as expressed by these claims, in general terms, some, but not necessarily all, of their features are:

One, my method comprises administering an anti-cancer substance via the patient's blood in line. It includes the steps of establishing a connection between the patient and a chamber containing the anti-cancer substance, and drawing the patient's blood into the chamber so that immune cells in the blood are treated by the anti-cancer substance to produce a beneficial response in the patient. After treating the immune cells, the patient's blood including the treated immune cells is returned to the patient. The connection is then terminated. The connection may be intravenously or subcutaneously. The anti-cancer substance may comprise an antibody, an antigen, an adjuvant material, or an immune activating substance.

Two, my method may be a batch or continuous process. In both the batch and continuous processes the dwell time in the chamber of the immune cells being treated may be on average a minimum of 15 seconds. Where blood is drawn from a patient's vein into the chamber, and after activating the immune cells, the patient's blood including the activated immune cells is returned to the patient intravenously. The immune cells may be white blood cells, which include effector cells, such as, for example, T-cells, NK cells, macrophages, monocytes, granulocytes, antigen presenting cells, and dendritic cells. The effector cell functions may include antibody binding, phagocytosis, cell lysis, antigen presentation, and release of intrinsic immune activating substances. The patient may be preconditioned by administering to the patient white blood cell growth factors.

Three, the chamber has an internal surface comprising a polymeric material that interacts with immune cells to stimulate effector cell functions. The internal surface may have multiple surfaces to which antibodies can attach themselves and to which immune cells can contact. The interiors of a plurality of micro tubules may provide the multiple surfaces. The plurality of micro tubules may be bundled into an array having opposed open ends and the anti-cancer substance may be attached to the internal surfaces of the micro tubules to contact with blood flowing through the micro tubules between the open ends. The internal surface attracts and holds individual antibodies. These individual antibodies are attached to the surface and oriented so Fc receptors on the individual antibodies are remote from the points of attachment to enable the receptors to bind to the immune cells in the patient's blood.

In my device for introducing into the blood of a patient an anti-cancer substance, the anti-cancer substance may be within the chamber prior to drawing the patient's blood into the chamber; or it may be introduced into the chamber after drawing the patient's blood into the chamber; or it may be introduced into the chamber concurrent with the introduction of the patient's blood into the chamber. The chamber may contain a first mechanism for establishing a connection between the patient and the chamber to enable blood to be withdrawn from the patient and treated by mixing with the anti-cancer substance, and a second mechanism for returning to the patient the patient's blood including the treated cells and then for terminating the connection. The first and second mechanisms may each establish an intravenous connection, or the second mechanism may establish a subcutaneous connection. The first and second mechanisms are operated to retain within the chamber the treated blood for a sufficient dwell time to enable the anti-cancer substance to be effective.

The chamber may have a port, and the second mechanism may be operably connected to the port while an intravenous connection is established for drawing the patient's blood into the chamber and for expelling treated blood from the chamber to return to the patient a mix of the patient's blood and the anti-cancer substance. The chamber may include a plurality of micro tubules bundled together.

In one embodiment of my device, the chamber has a first port into which blood from the patient is introduced and a second port adapted to be connected to a syringe to enable blood from the patient to be drawn into or expelled from the chamber through the first port upon operation of the syringe. Micro tubules may be parallel and are in communication via opposed open ends of the micro tubules with the first and second ports so that the patient's blood flows into or from the chamber through the open ends of the micro tubules in response to the operation of the syringe.

In another embodiment the chamber has a sidewall and opposed end walls enclosing an open space. First and second spaced apart ports are in the sidewall, a third port is in one end wall and a forth port is in the other end wall. An array of micro tubules are within the open space within the chamber in fluid communication with the first and second ports so that when the ports in the sidewall are connected to the patient blood from the patient flows through the chamber. The second and third ports are adapted to be placed in communication with a source of fluid in a manner enabling the fluid to flow through the open space concurrent with blood from the patient flowing through the chamber.

DESCRIPTION OF THE DRAWING

Some embodiments of my method and device are discussed in detail in connection with the accompanying drawing, which is for illustrative purposes only. This drawing includes the following figures (Figs.), with like numerals indicating like parts:

FIG. 2 is a perspective view of one embodiment of my device used in administering an anti-cancer substance according to one embodiment of my method.

FIG. 3 is a cross-sectional view of taken along line 3-3 of FIG. 2.

FIG. 4 is an enlarged fragmentary, cross-sectional view showing antibodies adhering to a surface within a chamber of the device illustrated in FIG. 2.

FIG. 5 is a fragmentary perspective view of a bundle of micro tubules within the device of FIG. 2.

FIG. 6 is a cross-sectional view of taken along line 6-6 of FIG. 2.

FIG. 7 is a perspective view of another embodiment of my device used in administering an anti-cancer substance according to a second embodiment of my method.

FIG. 8 is a cross-sectional view of taken along line 8-8 of FIG. 7.

FIG. 9 is a cross-sectional view of taken along line 9-9 of FIG. 8.

DETAILED DESCRIPTION OF SOME ILLUSTRATIVE EMBODIMENTS

The Method

Figure 1:
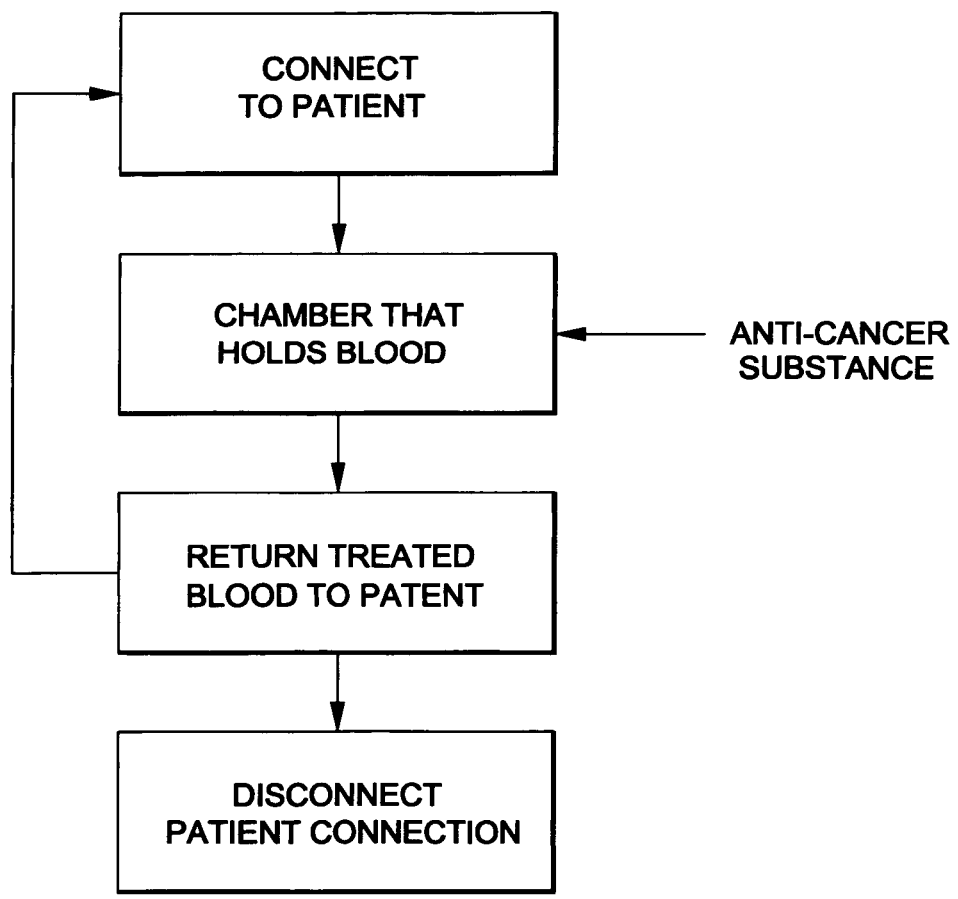
FIG. 1 is a diagram illustrating my method of administering ex vivo an anti-cancer substance via the patient's blood in line, then reintroducing the blood to the patient.

My method of administering an anti-cancer substance is via the patient's blood in line and ex vivo, resulting in sensitizing or activating immune cells in the patient's blood. My method comprises the steps of (1) establishing a connection between the patient and a chamber containing the anti-cancer substance, (2) drawing the patient's blood into the chamber so that immune cells in the blood are exposed to an anti-cancer substance, in some applications, activated by the anti-cancer substance to produce, for example, an immune response in the patient, and (3) after treating the immune cells, returning to the patient the patient's blood including the treated immune cells. My method may be a batch or continuous process, but regardless, the dwell time in the chamber of the immune cells being treated is on average a minimum of approximately 15 seconds. The connection may be intravenously or subcutaneously or both. For example, the blood may be drawn from a patient's vein into the chamber and after activating the immune cells of the blood returning intravenously the blood including the activated immune cells. The anti-cancer substance may be within the chamber prior to drawing the patient's blood into the chamber, or may be introduced into the chamber after drawing the patient's blood into the chamber, or may be introduced into the chamber concurrent with the introduction of the patient's blood into the chamber. Optionally, the patient may be preconditioned by administering to the patient white blood cell growth factors such as, for example, filgrastim. This preconditions the patient to increase their granulocyte count. Uniquely, neutrophils, a species of granulocytes, may be employed as anti-cancer effector cells according to my method.

The immune cells are typically white blood cells, including, for example, blood borne effector cells: T-cells, NK cells, macrophages, monocytes, granulocytes, antigen presenting cells, and dendritic cells. The anti-cancer substance may comprise an antibody, an antigen, an adjuvant material, or any other immune activating substance. Examples of anti-cancer substances are antibodies such as, for example, RITUXAN® (rituximab), an antigen such as, for example, CEA, and an adjuvant material such as, for example, interferon alpha. The chamber may have an internal surface comprising a polymeric material that interacts with immune cells to stimulate effector cell functions, such as, for example, antibody binding, phagocytosis, cell lysis, antigen presentation, and release of intrinsic immune activating substances. The chamber may have an internal structure that provides multiple surfaces to which antibodies can attach themselves and to which immune cells can contact, or provide a porous membrane through which molecules may pass from outside the membrane to attach to immune cells. For example, interiors of a plurality of micro tubules may provide such multiple surfaces. The chamber's internal surface may attract and hold individual antibodies. In such a case, individual antibodies may be attached to the surface and oriented so Fc receptors on the individual antibodies are remote from the points of attachment to enable the receptors to more likely to bind to the immune cells in the patient's blood. Drawing the patient's blood into the chamber thus pre-arms effector cells in the blood by attaching antibodies to effector cells via Fc receptors on the effector cells. The internal surface may, for example, be a polymeric material selected from the group consisting of polyvinyl chloride, cellulose acetate, and polysulfone.

FIG. 1 depicts my method. According to my method, while a patient is connected to a chamber containing the anti-cancer substance some of the patient's blood is introduced in line into the chamber to expose the blood to the anti-cancer substance within the chamber. Drawing the patient's blood into chamber produces different results depending on the cancer being treated and the anti-cancer substance used to sensitize, activate or pre-arm immune cells. One, it may pre-arm effector cells in the blood by attaching antibodies to the effector cells via Fc receptors on the effector cells. Or two, it may sensitize or activate antigen presenting or dendritic cells with which immune cells interact, or even convert such cells into effector cells. Or three, it may simply expose the cancer cells and/or immune cells to the anti-cancer substance. Or, it may do all of these. My method is unique in that the immune cells are selectively treated and specially exposed to the anti-cancer substance in a way that will make them more effective in fighting cancer.

Analogous to giving a bloodhound an item with the target scent, immune cells can be exposed, for example, to a target antigen by my method, with or without concurrent exposure to stimulatory or activating substances. Some prior art schemes employ removing blood from a patient's body to a laboratory where the effector cells in the blood are usually exposed to an adjuvant material at the same time as a target antigen. This occurs in vitro, and requires handling and manipulation of the patient's blood remotely and for a prolonged period after withdrawing the patient's blood, for example, over many hours to days, and typically in a separate laboratory. My method avoids these steps.

Without terminating the connection and after the patient's blood has been retained within the chamber for a sufficient period, for example, substantially from 10 to 90 minutes, the exposed blood including any activated antigen presenting cells and/or sensitized dendritic cells and/or activated effector cells is returned to the patient via the intravenous connection between the patient and my device 10 and then this connection is terminated. This procedure may be repeated periodically 1-3 times per week with treatment intervals of 1-2 days. Substantially from 50 to 1000 milliliters of blood are treated each time in a batch process where the patient's blood would flow into and fill the chamber containing the anti-cancer substance. The blood to be treated is retained therein for a predetermined period before returning the treated blood to the patient. For example, in one treatment session from about 1 to 3 batches of about 500 milliliters of blood are treated per day. Alternately, the patient's blood may be treated in a continuous flow system where blood constantly flows through the chamber containing the anti-cancer substance.

The Device

There are two embodiments of my device illustrated: one designated by the numeral 10 and shown in FIGS. 2 through 6, and the other designated by the numeral 10a and shown in FIGS. 7 through 10. The device 10 depicts a batch process system, and the device 10a depicts a continuous flow system. In general, both devices 10 and 10a are designed to manipulate the patient's immune system by taking into a chamber of my device in line and ex vivo an aliquot of the patient's blood and mixing it with an anti-cancer substance in a manner to sensitize, activate or pre-arm immune cells in the blood.

This could be achieved in either of two ways: In the first method, the anti-cancer substance is contained within the micro tubules 22, either in solution or electrostatically adhered to the walls of the micro tubules, or both. This exposes effector cells to, for example, an antigen and/or stimulatory agent as the cells marginate along the interior surfaces of the walls of the micro tubules or simply while circulating within the micro tubules. The embodiment 10 of my device is suited for conducting this first method. The embodiment 10a of my device is suited for conducting the second method, where the effector cells will be, for example, exposed to an antigen or activating substance in solution outside porous micro tubules 200a and penetrate sidewalls of these micro tubules.

FIGS. 2 Through 6

As illustrated in FIGS. 2 through 6, the embodiment of my device designed by the numeral 10 is a batch process system. The anti-cancer substance is introduced in line and ex vivo into the blood of a patient and held within a chamber 12 of the device 10 for a sufficient time period to condition the immune cells in the patient's blood to enhance their anti-tumor activities. My device includes a chamber 12 which may contain the anti-cancer substance placed in the chamber in advance. The chamber can be used with various techniques to accomplish the goal of either conditioning the patient's effector cells, or introducing an anti-cancer substance into the patient's blood, or both.

An IV tube 14 connected in a conventional manner to the patient's vein establishes an intravenous connection between the patient and the chamber 12 for drawing blood from the patient into the chamber. In this embodiment, for example, a syringe 16, is used to both draw blood into the chamber 12 and expel it from the chamber 12 returning it to the patient's blood stream including the sensitized, activated or pre-armed immune cells after an adequate dwell time within the chamber 12. The syringe 16 includes a plunger 16a the operation of which either draws blood into the chamber from the patient or expels it from the chamber into the patient. When the plunger 16a is manually pulled outward, a vacuum is created within the chamber 12 so the patient's blood flows into the chamber 16. When the plunger 16a is manually pushed inward, pressure within the chamber 12 is created to expel the treated patient's blood from the chamber 12 and inject the treated blood back into the patient's blood stream. When this treatment procedure is completed, then the IV tube 14 is detached from the patient and the intravenous connection is terminated.

In this embodiment, the chamber 12 may be an elongated, impermeable, plastic cylinder having a wall 12a made for example of polycarbonate, closed at both its opposed ends E1 and E2, and having a total volumetric capacity exceeding 50 milliliters and typically substantially from 50 to 1000 milliliters. Near the end E1 is an inlet/outlet port 18 to which an end E5 of the IV tube 14 is adapted to be detachably connected. Near the other end E2 is a connector port 20 that is adapted to be detachably connected to the outlet 16b of the syringe 16. As depicted in FIG. 4, the internal structure within my device 10 provides an extensive surface to which immune cells may be exposed. For example, an array of micro tubules 22 may be positioned within a fluid pathway from the port 18 to the port 20 so blood flow lengthwise from port to port through the lumens of the micro tubules. In the embodiment depicted in FIGS. 2 through 6, blood will enter one end of the lumens of the micro tubules 22 and flow through the lumens to the other ends of the micro tubules but not through the walls of the micro tubules or outside the micro tubules.

In this embodiment, an antibody introduced (before patient use) into the chamber 12 is attached to this extensive internal surface structure to which at numerous points thereof are attached individual molecules of antibodies that have a Fc cell attachment site oriented away from the surface into the lumen of the microtubule. The interior wall surface (in this embodiment, the internal lumens of the micro tubules 22) may be a polymeric material that electrostatically attracts and holds individual molecules, such as antibodies. A suitable polymeric material may be selected from a group consisting of polyvinyl chloride, cellulose acetate and polysulfone. Such an internal surface also attracts and holds individual antibodies, and these individual antibodies attach electrostatically to the surface and are oriented so that the Fc portions of the individual antibodies are remote from the points of attachment to the microtubule surface to better enable the Fc portions of the antibodies to bind to the Fc receptors of the effector cells in the patient's blood upon passage of the effector cells along the inner surface of the micro tubules 22 upon this blood being drawn through my device 10 by the operation of the syringe 16.

The array of micro tubules 22 may be in parallel to each other and to the central longitudinal axis X of the chamber 12. The micro tubules 22 are bundled together (FIG. 5) and the bundle is connected to the interior surface of the cylinder wall 12a by a pair of spaced apart barrier walls BW that hold the bundle in a fixed position within the chamber 12. The micro tubules 22 extend substantially from the one end E1 to the other end E2 of the chamber 12 with a small gap G (FIG. 6) between the ends E1 and E2 of the chamber 12 and opposed open ends E3 and E4 of the micro tubules 22. Thus the patient's blood is directed to flow along the micro tubules 22 from one end E3 or E4, as the case may be, between the ports 18 and 20. The micro tubules 22 are in communication via their opposed open ends E3 and E4 with the ports 18 and 20 so that the patient's blood only flows into and through the micro tubules in response to the operation of the syringe 16. Upon operating the syringe 16 to pull blood from the patient into my device 10, the patient's blood enters the ends E3 (FIG. 6) of the microtubule 22 and flows along the length of the micro tubules and to their other ends E4 near the port 20. Upon operating the syringe 16 to expel treated blood from my device 10, the treated blood flows along the length of the micro tubules 22 and out their ends E3 to exit the port 18. Each microtubule 22 may have a length substantially from 20 to 50 millimeters and an outside diameter substantially from 50 to 1000 microns to enable blood cells to enter and exit the micro tubules at their open ends. All the micro tubules 22 have substantially the same length. Suitable micro tubules 22 are made of materials such as cellulose acetate or polysulfone.

The embodiment illustrated, the polymeric internal surfaces of the micro tubules 22 can interact with effector cells in the patient's blood to stimulate effector cell functions by a phenomenon known as contact activation. Effector cells carried by the blood flowing through the micro tubules 22 will tend to approach the internal surfaces of the micro tubules and experience contact activation and exposure to molecules, such as antibodies, lining the internal surface of the micro tubules 22. The tendency for effector cells to preferentially flow next too and along the walls of the micro tubules is analogous to the situation within blood vessels in the patient's body, and is physiologic: a phenomenon known as margination.

FIGS. 7 Through 10

Figure 9A:
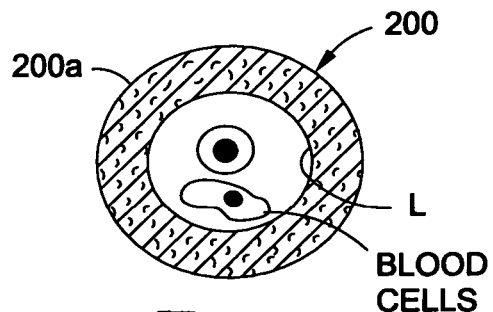
FIG. 9A is an enlarged cross-sectional view of a single micro tubule used in the embodiment of my device depicted in FIG. 7.

My device 10a is similar in some aspects to my device 10; however, as shown in FIG. 9A, in this embodiment micro tubules 200 having porous walls 200a (FIG. 9A) are employed. The porous walls 200a allow small diameter particles such as molecules with an average molecular weight from about 10,000 to 100,000 Daltons to pass therethrough, but prevent larger particles such as blood cells from passing through the porous walls. For example, the average pore diameter may range substantially from 1 to 2 microns.

My device 10a includes an array of such micro tubules 200, and each microtubule 22 may have a length substantially from 20 to 50 centimeters and an inside diameter substantially from 10 to 1000 microns. From about 200 to 1000 of such micro tubules 200 of substantially uniform length are bundled together to form an array that is retained within a chamber 104. The chamber 104 has a sidewall 104a closed by end walls 104b and 104c respectively at its opposed ends E5 and E6. Projecting from the sidewall 104a is a pair of spaced apart ports 100 and 102. Projecting from the end wall 104b along the longitudinal axis of the chamber 104 is a port 106 and projecting from the end wall 104c along the longitudinal axis of the chamber 104 is a port 108. The chamber 104 may be an elongated, impermeable, plastic cylinder made for example of polycarbonate, and have a total volumetric capacity exceeding 50 milliliters, typically substantially from 50 to 1000 milliliters.

The array of micro tubules 200 is disposed lengthwise along the longitudinal axis of the chamber 104 and it is sized to be offset from the inside surface of the chamber. This provides an open space S (FIG. 8) surrounding the array of micro tubules 200. The opposed open ends E7 and E8 of the array of micro tubules 200 are each respectively in fluid communication with manifolds M1 and M2. The manifold M1 is connected to the port 100 and the manifold M2 is connected to a port 102. The passageways or lumens L (FIG. 9A) of the micro tubules 200 allow liquid to flow in either direction lengthwise through the array and from the open ends of the micro tubules 200. The large particles such as blood cells are entrained in blood from the patient as it flows along the lumens L through my device 10a. Smaller particles may flow across the sidewall 104a into or from the open space S (FIG. 8) surrounding the array of micro tubules 200.

Figure 10:
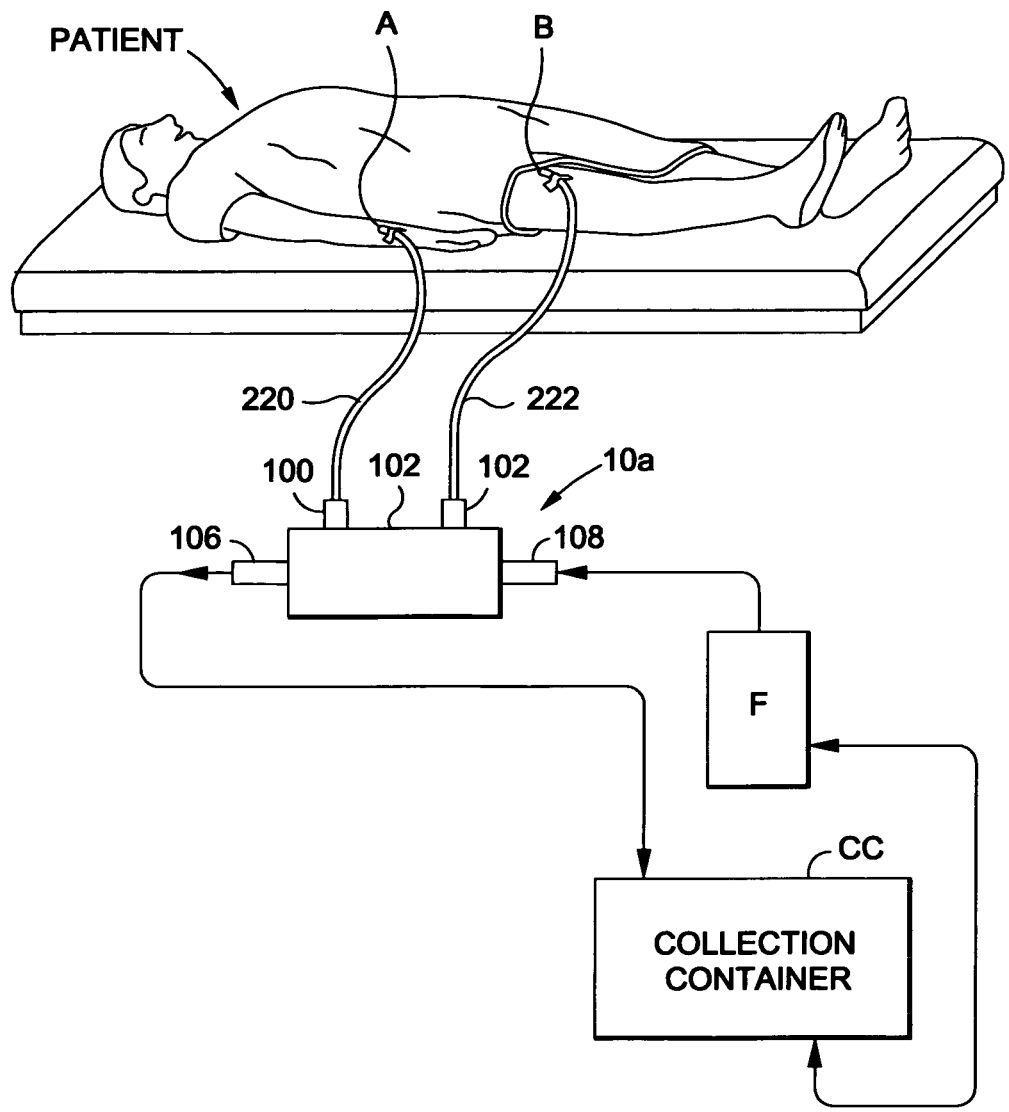
FIG. 10 illustrates using the embodiment of my device depicted in FIG. 7 according to the second embodiment of my method of administering an anti-cancer substance.

My device 10a may be used to conduct the method of administering an anti-cancer substance via the patient's blood in line and ex vivo as illustrated in FIG. 10. A vein A of a patient is connect via a conventional IV type line 220 to the port 100 so that the patient blood flows through the manifold M1 and the array of micro tubules 200 into and through the manifold M2 and out the port 102. One end of a line 222 is connected to the port 102 and its other end has a needle B inserted into the patient's intravenously. A fluid flows through the space S surrounding the array of micro tubules 200 concurrent with the flow of blood through the array. The fluid flow may be in the same direction or opposite the direction of flow through the array. The fluid may be held within a supply bottle F connected to the port 108 and fluid exiting my device 10a from the port 106 may be returned an stored in a collection container CC. The returned fluid may optionally be recycled to the supply bottle F. The fluid may be saline solution with or without an anti-cancer substance.

In the embodiment illustrated in FIG. 10 an anti-cancer substance is carried by the fluid flowing in the space S around of the array of micro tubules 200. The molecules of the anti-cancer substance penetrate the sidewall 104a and enter the interior of the micro tubules 200, or simply contact the membranes of effector cells marginated along the interior surface of the 200a walls of the micro tubules. Marginated effector cells can be exposed to antigen and adjuvant materials while the device 10a is thus attached in line to the patient.

EXAMPLES

The following are examples of illustrating the use of my method and device to treat cancer patients.

Example 1

A patient with NHL will be connected via his PICC line to my device. My device will have been prepared by instilling into it, before the patient is connected, a solution containing RITUXAN® (rituximab) antibody. The antibody will both remain in solution and be electrostatically attached to the inner surface of the micro tubules with the Fc portion of the antibodies oriented outward toward the lumen of the microtubule. Once the patient is connected, a syringe is connected to the device at port 20, and the patient's blood is drawn into and through the device by negative pressure applied by pulling the plunger back on the syringe. In so doing, the patient's WBCs, including granulocutes, T cells, NK cells, dendritic cells and macrophages will tend to marginate toward the walls of the micro tubules contained within the device. These cells will experience contact activation by virtue of their proximity to the plastic walls of the micro tubules, and display their Fc receptors. Because the device was preloaded with RITUXAN® (rituximab) antibody, the cells will pick up this antibody by binding it by the Fc portion with their Fc receptors. After an incubation period of about 10 to 90 minutes, the plunger of the syringe will then be depressed, creating a positive pressure and forcing the blood, with the now pre-armed and activated WBCs, back into the patient's circulation. The pre-armed and activated WBC's will then be able to localize to the NHL cells (and attach to their CD20 surface molecules) and destroy them by the mechanism of ADCC (antibody dependant cellular cytotoxicity) in the case of NK and T cells, or localize PMN's to the tumor, which will generate an inflammatory response at the tumor site. Additionally, by enriching and enabling the effector cells in this way, an autologous immune response is likely to be initiated at or within the tumor, allowing the body to develop its own, antigen specific response to the tumor. This autologous response may include the generation of the patient's own antibodies against the tumor, as well as the activation of effector cells specific for the tumor. On this note, dendritic cells or APCs (antigen presenting cells) will likewise be localized to the tumor, where further activation of effector cells, further antigenic processing and antigen presentation can take place, and the propagation of an inherent immune response can occur.

Example 2

While blood is within the micro tubules, a solution containing antigen and/or an adjuvant material is instilled in a solution surrounding the micro tubules. Exposure of the effector cells to the antigen and/or adjuvant occurs via micropores in the micro tubules. The process might be further enhanced using the fluid dynamic principle of countercurrent exchange, where fluid flowing in opposite directions, separated by a semipermeable membrane, experience enhanced exchange, or passage of molecules, across the membrane by virtue of stoichiometric principles. Blood (and hence the movement of effector cells) will move in a certain direction within the micro tubules; at first in one direction away from the patient and toward the syringe while the micro tubules are being filled. And then in the opposite direction toward the patient when the tubules are being emptied and blood and effector cells are being reinfused into the patient. In the chamber surrounding the micro tubules, fluid containing any of the substances described herein could be forced to flow in the opposite direction of the blood while the blood is flowing, thus employing the principle of countercurrent exchange.

As a specific example, carcinoembryonic antigen (CEA) is used in this way as a target antigen. CEA, which can be genetically engineered and produced, could be placed in solution, perhaps with an adjuvant material. The chamber 22a of my device contains the micro tubules 200, and fluid contained therein is outside of but in contact with the micro tubules. This chamber is preloaded with a CEA containing solution. This solution is circulated through the chamber, for counter current exchange, or could simply sit within the chamber. Connected to the patient, blood is drawn through the micro tubules within the device, as in example 1 above. Effector cells, marginated to the walls of the micro tubules are exposed to the CEA (and/or adjuvant) via the micropores within the micro tubules. Dendritic cells and other APCs, having experienced contact activation, or other manipulation, along the walls of the micro tubules, are able to phagocytose CEA by this exposure, and antigen-specific cells intrinsic within the patient's circulation (Tcells, NK cells and possibly B-cells) experience antigen exposure via their specific membrane receptors, which may alone be activating. The addition of adjuvant material to the solution enhances antigen-specific activation.

Example 3

Another approach using this device is to expose effector cells of the immune system to materials which can activate the inherent immune response to tumor. It is standard therapy to infuse an immune-activating material, interleukin-2 (IL-2), into the bloodstream of patients suffering from metastatic kidney cancer. Such therapy is profoundly toxic, but is known to enact cures in some patients. IL-2 is believed to act by stimulating an intrinsic immune response of the body against tumors. The known mechanism of the toxicity of this therapy is the widespread, systemic exposure of the vascular system to free IL-2, which causes the "vascular leak syndrome", and subsequent hypotension, renal failure, and sometimes death. Various schemes have been attempted to limit the toxicity of this therapy. One is to remove effector cells from the body and expose them to IL-2 in vitro, then instill them back into the body. Using the device, IL-2 or other adjuvant material in solution could be placed in the chamber surrounding the micro tubules 22a, and the effector cells of the patient are exposed to the material in the manner described above in Example 2 with minimal instillation of these often toxic materials back into the patient. Other materials known to stimulate the body's immune response could also be employed in this manner. A partial list includes the lymphokines (interleukins and interferons), complement, activating antibodies, fMLP, Freund's adjuvant, and Keyhole limpet antigen.

SCOPE OF THE INVENTION

The above presents a description of the best mode I contemplate of carrying out my method and of the manner and process of making and using my method and device, in such full, clear, concise, and exact terms as to enable a person skilled in the art to make and use. My method and device are, however, susceptible to modifications and alternate constructions from the illustrative embodiments discussed above which are fully equivalent. Consequently, it is not the intention to limit my method and device to the particular embodiments disclosed. On the contrary, my intention is to cover all modifications and alternate constructions coming within the spirit and scope of my method and device as generally expressed by the following claims, which particularly point out and distinctly claim the subject matter of my invention.

The invention claimed is:
1. A method of administering anti-cancer antibodies to a patient, comprising the steps of
    establishing an in line and ex vivo connection between the patient and a chamber containing the anti-cancer antibodies, said chamber comprising a plurality of parallel aligned polymeric micro tubules providing interior multiple surfaces to which individual antibodies are attached at points of attachment,
    said individual antibodies including Fc receptors that are oriented so the Fc receptors on individual antibodies are remote from their points of attachment to enable the Fc receptors to bind to the immune cells in the patient's blood,
    withdrawing blood from the patient into the chamber so that immune cells in the patient's blood flowing through the chamber are treated by the anti-cancer antibodies,
    said chamber providing an internal surface structure to which the anti-cancer antibodies are attached, said internal surface structure comprising a polymeric material that interacts with immune cells to stimulate effector cell functions,
    said blood flowing through the chamber and being returned to the patient without disconnection from the chamber, and
    after treating the patient's blood and returning to the patient the patient's blood including the treated immune cells, terminating the connection,
    said chamber having a pair of spaced apart ports, one port being adapted to be connected to the patient to enable blood to be withdrawn from the patient and flow into the chamber and be mixed with the anti-cancer antibodies in the chamber and the other port being adapted to enable the treated blood in the chamber to be returned to the patient,
    the patient's blood being retained in the chamber from 10 to 90 minutes and repeated periodically from 1 to 3 times per week with treatment intervals of from 1 to 2 days, whereby the immune cells in the blood contact and interact with the anti-cancer antibodies.

* * * * *